United States Patent
Wang et al.

(10) Patent No.: US 11,844,880 B2
(45) Date of Patent: Dec. 19, 2023

(54) RECOMBINANT HUMAN COLLAGEN-BASED MULTIFUNCTIONAL STENT COATING AND PREPARATION METHOD THEREOF

(71) Applicants: Sichuan University, Chengdu (CN); Shanxi Jinbo Bio-Pharmaceutical Co., Ltd, Taiyuan (CN)

(72) Inventors: Yunbing Wang, Chengdu (CN); Li Yang, Chengdu (CN); Rifang Luo, Chengdu (CN); Lu Lu, Chengdu (CN); Xia Yang, Chengdu (CN); Xingdong Zhang, Chengdu (CN)

(73) Assignees: Sichuan University, Chengdu (CN); Shanxi Jinbo Bio-Pharmaceutical Co., Ltd, Taiyuan (CN)

( * ) Notice: Subject to any disclaimer, the term of this patent is extended or adjusted under 35 U.S.C. 154(b) by 38 days.

(21) Appl. No.: 17/330,441

(22) Filed: May 26, 2021

(65) Prior Publication Data
US 2021/0369923 A1  Dec. 2, 2021

(30) Foreign Application Priority Data
May 26, 2020  (CN) .......................... 202010452431.7

(51) Int. Cl.
*A61L 31/10* (2006.01)
*B05D 3/10* (2006.01)
(52) U.S. Cl.
CPC .............. *A61L 31/10* (2013.01); *B05D 3/104* (2013.01); *B05D 3/107* (2013.01); *A61L 2300/252* (2013.01); *A61L 2420/02* (2013.01)
(58) Field of Classification Search
CPC .... A61L 33/0029; A61L 31/148; A61L 31/10; A61L 27/24
See application file for complete search history.

(56) References Cited

U.S. PATENT DOCUMENTS

| | | | |
|---|---|---|---|
| 5,811,151 A * | 9/1998 | Hendriks | A61L 33/0029 427/407.1 |
| 2006/0147501 A1* | 7/2006 | Hillas | A61L 27/24 424/443 |
| 2007/0244569 A1* | 10/2007 | Weber | A61L 31/148 623/1.42 |

OTHER PUBLICATIONS

Wang et al. ("Production of recombinant collagen: state of the art and challenges", 2017, Engineering Biology, vol. 1, Iss. 1., pp. 18-23 (Year: 2017).*

* cited by examiner

*Primary Examiner* — Dah-Wei D. Yuan
*Assistant Examiner* — Andrew J Bowman
(74) *Attorney, Agent, or Firm* — Bayramoglu Law Offices LLC

(57) ABSTRACT

A recombinant human collagen-based multifunctional stent coating and a preparation method thereof are provided. The preparation method includes (1) activating a substrate material; (2) placing the activated substrate material in an amino compound-containing solution for a reaction to obtain an aminated substrate material; (3) placing the aminated substrate material in a polyanion electrolyte solution for a reaction, and cleaning with deionized water. The recombinant human collagen-based multifunctional stent coating prepared by the present invention effectively improves the anticoagulation and rapid endothelialization performance of biomaterials, such as vascular stent materials, and reduces the late thrombosis and restenosis problems existing in current stent materials.

14 Claims, 2 Drawing Sheets
Specification includes a Sequence Listing.

RECOMBINANT HUMAN COLLAGEN-BASED MULTIFUNCTIONAL STENT COATING AND PREPARATION METHOD THEREOF

CROSS REFERENCE TO THE RELATED APPLICATIONS

This application is based upon and claims priority to Chinese Patent Application No. 202010452431.7, filed on May 26, 2020, the entire contents of which are incorporated herein by reference.

TECHNICAL FIELD

The present invention belongs to the technical field of medical materials, and in particular to a recombinant human collagen-based multifunctional stent coating and a preparation method thereof.

BACKGROUND

With increasing pressure, and irregular work, rest and diet in people's daily life, the death rate caused by cardiovascular diseases in China has exceeded 40%, which has surpassed tumors as the number one killer disease related death. This threatens the safety of human life. For a long time, cardiovascular materials have faced the problems of unsatisfactory anticoagulation and incomplete endothelialization. Excellent surface anticoagulation properties and accelerated in situ endothelialization are key to successful blood-contacting materials. Minimally invasive, efficient, and safe stenting has become the primary treatment for cardiovascular diseases.

Currently, drug-coated metallic vascular stents play a supporting role in clinical practice. The implantation of foreign bodies, however, causes thrombosis and restenosis. Besides, the drug coating inhibits the growth of intima and endothelium. The coating design strategy of existing drug-eluting stents is commonly used in the design of all-degraded vascular stents. The existing stent coating prevents intimal over-proliferation while hindering the overall function and structural regeneration of endothelium.

Therefore, it may still potentially lead to late thrombosis due to insufficient regeneration of endothelial covering layer. At present, it is one of the necessary conditions to achieve perfect regeneration of vascular tissue structure and function by further optimization or surface modification of drug-loaded coating and accelerating the completion of vascular endothelialization while improving the anticoagulation performance. However, there is no report on the application of recombinant human collagen in the construction of multifunctional stent coating.

SUMMARY

In view of the above problems existing in the prior art, the present invention provides a recombinant human collagen-based multifunctional stent coating and a preparation method thereof, which can effectively improve the anticoagulation and rapid endothelialization performance of biomaterials such as vascular stent materials, and potentially reduce the late thrombosis and restenosis problems existing in the current stent materials.

In order to achieve the above objective, the technical solution adopted by the present invention to solve the technical problem is as follows.

A preparation method of a recombinant human collagen-based multifunctional stent coating includes the following steps:

(1) placing a substrate material in an activator solution for a reaction to obtain an activated substrate material;

(2) placing the activated substrate material in an amino compound-containing solution for a reaction to obtain an aminated substrate material;

(3) placing the aminated substrate material in a polyanion electrolyte solution for a reaction, and cleaning with deionized water;

(4) placing the product obtained in step (3) in a polycation electrolyte solution for a reaction, and cleaning with deionized water, where, the polycation electrolyte solution is a recombinant human collagen solution; and (5) repeating step (3) to step (4) for 3-15 times at room temperature using the aminated substrate material obtained in step (2) as a substrate, to obtain the final product. In this step, the recombinant human collagen is introduced into the coating in a layer-by-layer assembly manner to further improve the assembly amount of the polyanion electrolyte, so as to achieve the anticoagulant performance and rapid endothelialization performance of the coating.

Further, step (1) specifically includes: placing the substrate material in the activator solution with a concentration of 0.5-10 mg/mL, performing the reaction at room temperature for 30 min-4 h, and cleaning for 3-5 times to obtain the activated substrate material; where, an activator is a carbodiimide/succinimide (EDC/NHS) system or dopamine hydrochloride (DPA).

Further, when the activator is the EDC/NHS system, the activation process is as follows: immersing the substrate material in a 2-(N-morpholino) ethanesulfonic acid (MES) buffer solution containing 0.5-10 mg/mL EDC for 10 min-2 h, and transferring into a 0.5-10 mg/mL NHS solution for an activation treatment for 30 min-2 h. Preferably, the activation process includes immersing the substrate material in the MES buffer containing 1 mg/mL EDC for 15 min, and transferring into a 1.5 mg/mL NHS solution for the activation treatment for 1 h.

Further, step (2) specifically includes: placing the activated substrate material in the amino compound-containing solution with a concentration of 5-20 mg/mL, and performing the reaction at room temperature for 2-4 h; where, the amino compound is a substance carrying multiple primary amino groups, including but not limited to polyethylenimine, carboxymethyl chitosan, polylysine, polyarginine, polyethylenediamine, etc.

Further, step (3) specifically includes: placing the aminated substrate material in the polyanion electrolyte solution with a concentration of 0.1-5 mg/mL and a pH value of 2-9, performing the reaction at room temperature for 5 min-1 h, and cleaning with deionized water for 3-5 times. Preferably, the aminated substrate material is placed in the polyanion electrolyte solution with the concentration of 0.5 mg/mL and the pH value of 5, and the reaction is performed at room temperature for 20 min, followed by cleaning with deionized water for 3-5 times.

Further, the polyanion electrolyte in step (3) is chondroitin sulfate, dermatan sulfate, keratin sulfate, hyaluronic acid, heparin, polyglutamic acid or deoxyribonucleic acid.

Further, step (4) specifically includes: placing the product obtained in step (3) in the polycation electrolyte solution with a concentration of 0.1-5 mg/mL and a pH value of 2-9, performing the reaction at room temperature for 5 min-1 h, and cleaning with deionized water for 3-5 times. Preferably, the product obtained in step (3) is placed in the polycation electrolyte solution with the concentration of 0.5 mg/mL and the pH value of 5, and the reaction is performed at room temperature for 30 min, followed by cleaning with deionized water for 3-5 times.

Further, in step (4), a primary structure of the recombinant human collagen is O-free (hydroxyproline), has cellular adhesion properties, and is preferably a collagen tripeptide fragment (GER) containing cellular adhesion functions, but does not contain collagen-mimetic peptides (GFOGER, as shown in SEQ ID NO. 2) that specifically bind to α2β1 integrin on a platelet surface.

Further, a core sequence of an amino acid sequence of the recombinant human collagen is GERGAPGFRGPAGPN-GIPGEKGPAGERGAP (as shown in SEQ ID NO. 1), and the core sequence may be modified, and the sites and groups where the modification is performed include but are not limited to a mercapto terminal (—SH), a terminal double bond and methacrylate.

Further, the substrate material is a metal-based biomaterial or a polymer-based biomaterial.

The metal-based biomaterial includes but is not limited to magnesium and magnesium alloy, iron and iron alloy, stainless steel, nickel-titanium (Ni—Ti) alloy, cobalt-chromium (Co—Cr) alloy, titanium and titanium alloy.

The polymer-based biomaterial includes but is not limited to chitosan, polylactic acid, polycaprolactone, polyurethane, polytetrafluoroethylene, silicone rubber, polyester, glycolide-lactide or polytrimethylene carbonate.

The recombinant human collagen-based multifunctional stent coating and the preparation method thereof provided by the present invention have the following advantages.

In the present invention, the substrate material is activated by an activator, and various functional groups such as carboxyl, aldehyde and hydroxyl are introduced into the surface of the substrate material to obtain the activated substrate material. The activated substrate material is placed in an amino compound-containing solution, and the carboxyl, aldehyde and amino groups on the surface of the activated substrate material form covalent bonds and hydrogen bonds, so that the surface of the substrate material carries amino functional groups to form the aminated substrate material. The aminated substrate material is placed in the polyanion electrolyte, the carboxyl group and hydroxyl group of the polyanion electrolyte are fixed on the surface of the aminated substrate material through electrostatic interaction, and a small amount of covalent bonds and hydrogen bonds reacting with the amino groups. Then the obtained product is placed in the polycation electrolyte. The polycation electrolyte adhere to the substrate material by electrostatic interaction between the polycation electrolyte and the polyanion electrolyte. Preferably, the polycation electrolyte is the recombinant human collagen solution. The recombinant human collagen forms covalent bonds and hydrogen bonds with the carboxyl and hydroxyl groups carried by the polyanion electrolyte, thereby improving the stability of recombinant human collagen on the material surface. Finally, layer by layer self-assembly method is used to alternately deposit the polyanion electrolyte and polycation electrolyte onto the aminated substrate material to achieve in situ modification of vascular stent.

In this application, the polycation electrolyte is the recombinant human collagen with anticoagulant property, which has high affinity for endothelial cells, and its sequence design avoids the new collagen structure of platelet binding site. It is a customized collagen material that can be used for the modification of cardiovascular materials, and its significance is reflected in that the recombinant human collagen not only has extremely low immune rejection, but also has remarkable anticoagulant properties. The traditional collagen is a mixture of various types of collagen, and it is difficult to remove the O-containing residues in the structure, resulting in the coagulation of DNA fragments in platelets and thus making complete removal of animal amino acid groups difficult in immune response. The primary structure of the recombinant human collagen designed by the present invention does not contain O, and the above problem does not occur.

DETAILED DESCRIPTION OF THE EMBODIMENTS

Example 1

Figure 1A:
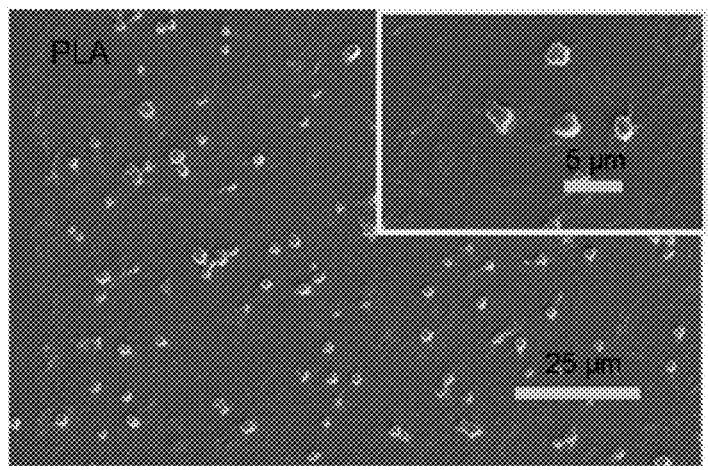
FIG. 1A is a scanning electron microscope (SEM) image showing a platelet adhesion experiment of a control group.

A preparation method of a recombinant human collagen-based multifunctional stent coating includes the following steps.

(1) A pretreated Co—Cr alloy material is treated in an MES buffer containing 0.5 mg/mL EDC for 30 min, then transferred into a 0.5 mg/mL NHS solution for activation for 30 min.

(2) The product obtained in step (1) is placed in a polyethyleneimine solution with a concentration of 5 mg/mL and a pH value of 8, and reacted for 2 h at room temperature.

(3) The product obtained in step (2) is placed in a chondroitin sulfate solution with a concentration of 0.1 mg/mL and a pH value of 3, and reacted for 5 min at room temperature.

(4) The product obtained in step (3) is placed in a recombinant human type III collagen solution with a concentration of 0.1 mg/mL and a pH value of 3, and reacted for 5 min at room temperature. The amino acid sequence of the recombinant human type III collagen is GERGAPG-FRGPAGPNGIPGEKGPAGERGAP.

(5) Step (3) to step (4) are repeated for 3 times at room temperature using the product obtained in step (2) as a substrate, to obtain the target coating.

Example 2

A preparation method of a recombinant human collagen-based multifunctional stent coating includes the following steps.

(1) A pretreated Co—Cr alloy material is treated in an MES buffer containing 5 mg/mL EDC for 2 h, then transferred into a 5 mg/mL NHS solution for activation for 2 h.

(2) The product obtained in step (1) is placed in a polylysine solution with a concentration of 10 mg/mL and a pH value of 8, and reacted for 2 h at room temperature.

(3) The product obtained in step (2) is placed in a chondroitin sulfate solution with a concentration of 2 mg/mL and a pH value of 4, and reacted for 30 min at room temperature.

(4) The product obtained in step (3) is placed in a recombinant human type III collagen solution with a concentration of 2 mg/mL and a pH value of 4, and reacted for 30 min at room temperature. The amino acid sequence of the recombinant human type III collagen is GERGAPG-FRGPAGPNGIPGEKGPAGERGAP.

(5) Step (3) to step (4) are repeated for 6 times at room temperature using the product obtained in step (2) as a substrate, to obtain the target coating.

Example 3

A preparation method of a recombinant human collagen-based multifunctional stent coating includes the following steps.

(1) A pretreated chitosan material is treated in a 2 mg/mL DPA solution, and reacted for 2 h at room temperature.

(2) The product obtained in step (1) is placed in a polyethylenediamine solution with a concentration of 10 mg/mL and a pH value of 7.4, and reacted for 3 h at room temperature.

(3) The product obtained in step (2) is placed in a heparin solution with a concentration of 2 mg/mL and a pH value of 6, and reacted for 30 min at room temperature.

(4) The product obtained in step (3) is placed in a recombinant human type III collagen solution with a concentration of 2 mg/mL and a pH value of 6, and reacted for 30 min at room temperature. The amino acid sequence of the recombinant human type III collagen is GERGAPG-FRGPAGPNGIPGEKGPAGERGAP.

(5) Step (3) to step (4) are repeated for 10 times at room temperature using the product obtained in step (2) as a substrate, to obtain the target coating.

Example 4

A preparation method of a recombinant human collagen-based multifunctional stent coating includes the following steps.

(1) A polylactic acid material is treated in a 4 mg/mL DPA solution, and reacted for 30 min at room temperature.

(2) The product obtained in step (1) is placed in a polylysine solution with a concentration of 5 mg/mL and a pH value of 7, and reacted for 2 h at room temperature.

(3) The product obtained in step (2) is placed in a hyaluronic acid solution with a concentration of 5 mg/mL and a pH value of 4, and reacted for 10 min at room temperature.

(4) The product obtained in step (3) is placed in a recombinant human type III collagen solution with a concentration of 5 mg/mL and a pH value of 7, and reacted for 30 min at room temperature. The amino acid sequence of the recombinant human type III collagen is GERGAPG-FRGPAGPNGIPGEKGPAGERGAP.

(5) Step (3) to step (4) are repeated for 15 times at room temperature using the product obtained in step (2) as a substrate, to obtain the target coating.

Example 5

A preparation method of a recombinant human collagen-based multifunctional stent coating includes the following steps.

(1) A polylactic acid material is treated in an MES buffer containing 1 mg/mL EDS for 15 min, then transferred into a 1.5 mg/mL NHS solution for activation for 1 h.

(2) The product obtained in step (1) is placed in a carboxymethyl chitosan solution with a concentration of 10 mg/mL and a pH value of 7.4, and reacted for 3 h at room temperature.

(3) The product obtained in step (2) is placed in a hyaluronic acid solution with a concentration of 1 mg/mL and a pH value of 6, and reacted for 20 min at room temperature.

(4) The product obtained in step (3) is placed in a recombinant human type III collagen solution with a concentration of 1 mg/mL and a pH value of 6, and reacted for 30 min at room temperature. The amino acid sequence of the recombinant human type III collagen is GERGAPG-FRGPAGPNGIPGEKGPAGERGAP.

(5) Step (3) to step (4) are repeated for 6 times at room temperature using the product obtained in step (2) as a substrate, to obtain the target coating.

Example 6

A preparation method of a recombinant human collagen-based multifunctional stent coating includes the following steps.

(1) A pretreated magnesium alloy material is treated in a 5 mg/mL DPA solution, and reacted for 1 h at room temperature.

(2) The product obtained in step (1) is placed in a polyarginine solution with a concentration of 10 mg/mL and a pH value of 7.4, and reacted for 30 min at room temperature.

(3) The product obtained in step (2) is placed in a polyglutamic acid solution with a concentration of 2 mg/mL and a pH value of 5, and reacted for 40 min at room temperature.

(4) The product obtained in step (3) is placed in a recombinant human type III collagen solution with a concentration of 2 mg/mL and a pH value of 5, and reacted for 30 min at room temperature. The amino acid sequence of the recombinant human type III collagen is GERGAPG-FRGPAGPNGIPGEKGPAGERGAP.

(5) Step (3) to step (4) are repeated for 10 times at room temperature using the product obtained in step (2) as a substrate, to obtain the target coating.

Experimental Example

1. Platelet Adhesion Experiment

The recombinant human collagen-based multifunctional stent coating prepared in example 4 is mixed with platelet rich plasma and incubated for 1 h. The polylactic acid (PLA) substrate material is used as a control group. The adhesion of platelets on the multifunctional stent coating and the PLA substrate material is observed by scanning electron microscope. The results are shown in FIG. 1.

Figure 1B:
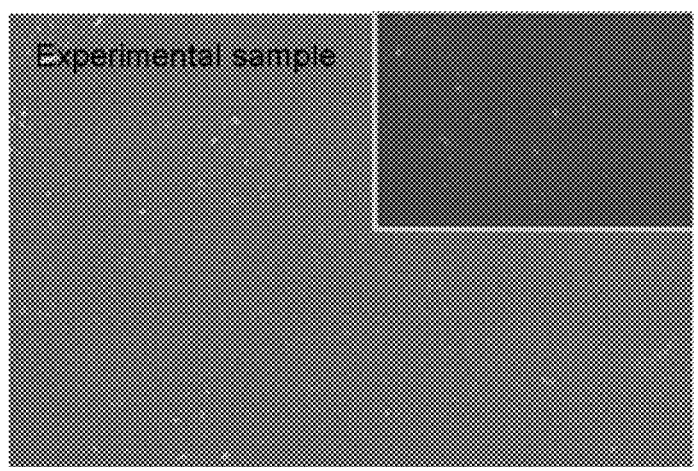
FIG. 1B is a SEM image showing a platelet adhesion experiment of the multifunctional stent coating prepared in example 4.

FIG. 1 shows that there are a large number of platelets attached on the surface of the PLA substrate material in the control group with high degree of activation, while there is basically no platelet adhesion and activation on the surface of the multifunctional stent coating, which indicates that the recombinant human collagen-based multifunctional stent coating prepared by the present invention has excellent anticoagulant function.

2. Endothelial Cell Adhesion Experiment

The recombinant human collagen-based multifunctional stent coating prepared in example 5 is co-cultured with endothelial cells, and the PLA substrate material is used as a control group to observe the growth of endothelial cells on the surface of the multifunctional stent coating and the surface of the PLA substrate material. The results are shown in FIG. 2.

Figure 2A:
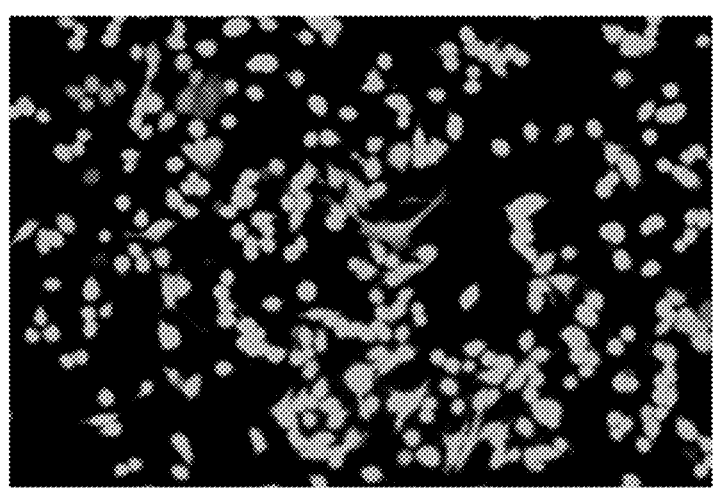
FIG. 2A a diagram showing fluorescent staining results of endothelial cells in the control group.
Figure 2B:
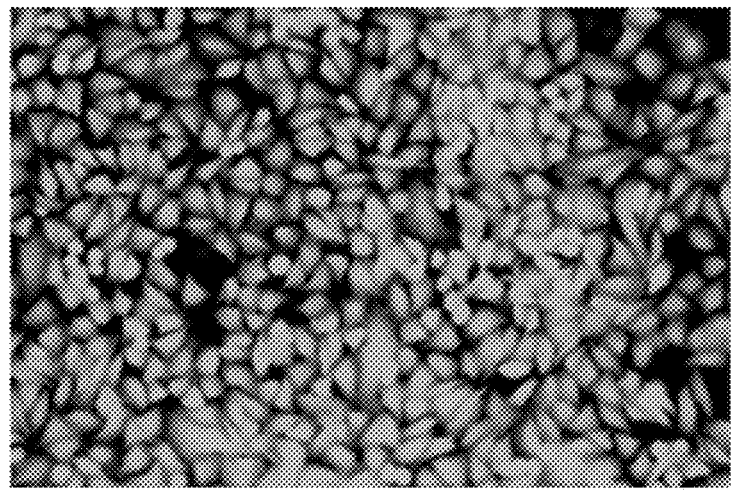
FIG. 2B is a diagram showing fluorescent staining results of endothelial cells in the multifunctional stent coating prepared in example 5.

In FIG. 2, the left image shows the control group, and the right image shows the experimental group. FIG. 2 shows that the multifunctional stent coating can effectively promote the adhesion and growth of endothelial cells.

What is claimed is:

1. A preparation method of a recombinant human collagen-based multifunctional stent coating, comprising the following steps:
   (1) placing a substrate material in an activator solution for a first reaction to obtain an activated substrate material;
   (2) placing the activated substrate material in an amino compound-containing solution for a second reaction to obtain an aminated substrate material;
   (3) placing the aminated substrate material in a polyanion electrolyte solution for a third reaction to obtain a first treated product, and cleaning the first treated product with deionized water to obtain a cleaned product, wherein the polyanion electrolyte solution comprises chondroitin sulfate, dermatan sulfate, keratin sulfate, polyglutamic acid or deoxyribonucleic acid;
   (4) placing the cleaned product obtained in step (3) in a polycation electrolyte solution for a fourth reaction to obtain a second treated product, and cleaning the second treated product with deionized water, wherein the polycation electrolyte solution is a recombinant human type III collagen solution, wherein a primary structure of a recombinant human collagen in the recombinant human type III collagen solution is hydroxyproline-free and has cellular adhesion properties, and the primary structure does not contain collagen-mimetic peptides that specifically bind to α2β1 integrin on a platelet surface; and
   (5) repeating step (3) to step (4) for 3-15 times at room temperature using the aminated substrate material obtained in step (2) as a substrate to obtain the recombinant human collagen-based multifunctional stent coating.

2. The preparation method of the recombinant human collagen-based multifunctional stent coating according to claim 1, wherein an activator of the activator solution in step (1) is a carbodiimide/succinimide (EDC/NHS) system or dopamine hydrochloride (DPA).

3. The preparation method of the recombinant human collagen-based multifunctional stent coating according to claim 1, wherein an amino compound of the amino compound-containing solution in step (2) is a substance carrying a plurality of primary amino groups.

4. The preparation method of the recombinant human collagen-based multifunctional stent coating according to claim 1, wherein step (3) specifically comprises:
   placing the aminated substrate material in the polyanion electrolyte solution with a concentration of 0.1-5 mg/mL and a pH value of 2-9, performing the third reaction at room temperature for 5 min-1 h, and cleaning the first treated product with deionized water for 3-5 times.

5. The preparation method of the recombinant human collagen-based multifunctional stent coating according to claim 1, wherein step (4) specifically comprises:
   placing the cleaned product obtained in step (3) in the polycation electrolyte solution with a concentration of 0.1-5 mg/mL and a pH value of 2-9, performing the fourth reaction at room temperature for 5 min-1 h, and cleaning the second treated product with deionized water for 3-5 times.

6. The preparation method of the recombinant human collagen-based multifunctional stent coating according to claim 1, wherein an amino acid sequence of the recombinant human collagen comprises a collagen tripeptide fragment (GER), and wherein the collagen-mimetic peptides are as shown in SEQ ID NO: 2.

7. The preparation method of the recombinant human collagen-based multifunctional stent coating according to claim 6, wherein a core sequence of the recombinant human collagen is SEQ ID NO: 1.

8. A recombinant human collagen-based multifunctional stent coating, wherein the recombinant human collagen-based multifunctional stent coating is prepared by the preparation method according to claim 1.

9. The recombinant human collagen-based multifunctional stent coating according to claim 8, wherein an activator of the activator solution in step (1) is a carbodiimide/succinimide (EDC/NHS) system or dopamine hydrochloride (DPA).

10. The recombinant human collagen-based multifunctional stent coating according to claim 8, wherein an amino compound of the amino compound-containing solution in step (2) is a substance carrying a plurality of primary amino groups.

11. The recombinant human collagen-based multifunctional stent coating according to claim 8, wherein step (3) specifically comprises: placing the aminated substrate material in the polyanion electrolyte solution with a concentration of 0.1-5 mg/mL and a pH value of 2-9, performing the third reaction at room temperature for 5 min-1 h, and cleaning the first treated product with deionized water for 3-5 times.

12. The recombinant human collagen-based multifunctional stent coating according to claim 8, wherein step (4) specifically comprises: placing the cleaned product obtained in step (3) in the polycation electrolyte solution with a concentration of 0.1-5 mg/mL and a pH value of 2-9, performing the fourth reaction at room temperature for 5 min-1 h, and cleaning the second treated product with deionized water for 3-5 times.

13. The recombinant human collagen-based multifunctional stent coating according to claim 8, wherein an amino acid sequence of the recombinant human collagen comprises a collagen tripeptide fragment (GER), and wherein the collagen-mimetic peptides are as shown in SEQ ID NO: 2.

14. The recombinant human collagen-based multifunctional stent coating according to claim 13, wherein a core sequence of the recombinant human collagen is SEQ ID NO: 1.

* * * * *

```
                        SEQUENCE LISTING

<160> NUMBER OF SEQ ID NOS: 2

<210> SEQ ID NO 1
<211> LENGTH: 30
<212> TYPE: PRT
<213> ORGANISM: Artificial Sequence
<220> FEATURE:
<223> OTHER INFORMATION: The sequence is synthesized.

<400> SEQUENCE: 1

Gly Glu Arg Gly Ala Pro Gly Phe Arg Gly Pro Ala Gly Pro Asn Gly
1               5                   10                  15

Ile Pro Gly Glu Lys Gly Pro Ala Gly Glu Arg Gly Ala Pro
            20                  25                  30

<210> SEQ ID NO 2
<211> LENGTH: 6
<212> TYPE: PRT
<213> ORGANISM: Artificial Sequence
<220> FEATURE:
<223> OTHER INFORMATION: The sequence is synthesized.
<220> FEATURE:
<221> NAME/KEY: MISC_FEATURE
<222> LOCATION: (1)..(6)
<223> OTHER INFORMATION: Xaa = hydroxyproline

<400> SEQUENCE: 2

Gly Phe Xaa Gly Glu Arg
1               5
```